United States Patent
Suttor et al.

(10) Patent No.: US 6,709,694 B1
(45) Date of Patent: Mar. 23, 2004

(54) COLORING CERAMICS BY WAY OF IONIC OR COMPLEX-CONTAINING SOLUTIONS

(75) Inventors: Daniel Suttor, Seefeld (DE); Holger Hauptmann, Sindelsdorf (DE); Robert Schnagl, Landsberg (DE); Sybille Frank, Seefeld (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 09/890,690

(22) PCT Filed: Feb. 4, 2000

(86) PCT No.: PCT/EP00/00910
§ 371 (c)(1),
(2), (4) Date: Sep. 26, 2001

(87) PCT Pub. No.: WO00/46168
PCT Pub. Date: Aug. 10, 2000

(30) Foreign Application Priority Data

Feb. 4, 1999 (DE) .......................... 199 04 522

(51) Int. Cl.⁷ .......................... B05D 3/02; A61L 27/00; A61C 13/00
(52) U.S. Cl. ...................... 427/2.26; 427/2.1; 427/2.24; 427/376.3; 427/2.27; 427/2.29; 427/431; 427/443.2; 427/372.2; 427/376.2
(58) Field of Search .......................... 427/372.2, 376.2, 427/376.3, 2.1, 2.24, 2.26, 2.27, 2.29, 427, 431, 443.2

(56) References Cited

U.S. PATENT DOCUMENTS

| | | | | |
|---|---|---|---|---|
| 5,011,403 A | * | 4/1991 | Sadoun et al. ................. | 433/8 |
| 5,091,033 A | * | 2/1992 | Nakabayashi et al. ...... | 156/316 |
| 5,565,152 A | * | 10/1996 | Od en et al. ................ | 264/162 |
| 5,618,585 A | * | 4/1997 | Hechler et al. ............. | 427/162 |

FOREIGN PATENT DOCUMENTS

| | | |
|---|---|---|
| DE | 2 012 304 | 9/1971 |
| DE | A1-3424777 | 1/1985 |
| DE | A1-3435181 | 8/1985 |
| DE | A1-3435182 | 8/1985 |
| DE | C1-4320072 | 5/1994 |
| DE | C1-19619165 | 9/1997 |
| DE | C1-19619168 | 10/1997 |
| DE | A1-19625236 | 1/1998 |
| EP | A1329565 | 8/1989 |
| EP | A1816305 | 1/1998 |
| GB | 421872 | 1/1935 |
| WO | WO 97/49650 A1 | 12/1997 |

OTHER PUBLICATIONS

Industrie Diamanten Rundschau IDR Feb. 1993 "Aluminium und Zirkonoxidkeramik in der Medizin."
Pamphlet relating to the Cerec System—Okonomie durch Technologie.
Pamphlet relating to the Procera system.

* cited by examiner

Primary Examiner—Shrive P. Beck
Assistant Examiner—Jennifer Kolb Michener
(74) Attorney, Agent, or Firm—Birch, Stewart, Kolasch & Birch, LLP

(57) ABSTRACT

The invention relates to the coloring of ceramics by means of ionic or complex-containing solutions. Solutions preferred for this contain defined concentrations of at least one of the salts or complexes of the rare earth elements or the elements of the subgroups. The invention also relates to a kit, which comprises at least one stock bottle with such a coloring solution, a receptacle for the coloring as well as optionally a screen.

14 Claims, No Drawings

COLORING CERAMICS BY WAY OF IONIC OR COMPLEX-CONTAINING SOLUTIONS

This application is the national phase under 35 U.S.C. §371 of PCT International Application No. PCT/EP00/00910 which has an International filing date of Feb. 4, 2000, which designated the United States of America and was not published in English.

FIELD OF THE INVENTION

The invention relates to the colouring of ceramics by means of ionic or complex-containing solutions. The invention relates in particular to the colouring of dental ceramics based on zirconium oxide by means of solutions of rare earth metals and subgroup elements.

BACKGROUND OF THE RELATED ART

Ceramics are much valued, because of their physical properties, in the construction of high-quality dentures. Aluminium and zirconium oxide ceramics have long been the materials of choice in the medical field (Reprint from Industrie Diamanten Rundschau, IDR February 1993, "Aluminium- und Zirkonoxidkeramik in der Medizin"). There are a number of publications in the dental field which deal with the use of ceramics for the preparation of prostheses. Various ceramic systems are also already available on the dental market (CEREC, Fa. Siemens; Procera, Fa. Nobel-Biocare).

In the dental field in particular, however, it is not only the mechanical parameters that play a major role, but also specially the aesthetics. Translucence and coloration of the framework or facing ceramics are important, in order to allow the patient to achieve a natural appearance for his dentures.

Dentures are normally prepared from a framework and a facing.

In the case of the systems known up until now, only a superficial individual colouring of the basic framework can be carried out by the dental technician, the aesthetic design possibilities being limited.

In order to achieve a natural appearance of the prosthesis, the tooth colour and the translucence must be simulated over several layers, beginning with the framework.

The natural appearance of a prosthesis is guaranteed by as high as possible a free path length $z=x+y+m$ of the incident light through the layer (x) of the facing ceramic and the layer (m) of the framework ceramic and optionally an intermediate layer (y).

In order to change the basic shade of the framework ceramic, conventional systems must work with colouring intermediate layers, for example opaquer liners, which display no, or greatly reduced, translucence; the free path length of the light decreases by the thickness of the framework ceramic (m) and of the intermediate layer (y) to $z=x$. A description of this procedure can be found in e.g. the instructions issued by Vita for the use of the Vita-Dur system □ or by DUCERA for the ALL Ceram system.

Such systems use, as intermediate layer, dye pastes or dye suspensions, which are applied to the framework by the dental technician in several procedures and are finally fired in the oven.

This process is not only time-consuming, but also cost-intensive.

SUMMARY OF THE INVENTION

The object of the invention is thus to provide a system for the colouring of ceramics, in particular ceramic dentures, which guarantees an optimum aesthetic appeal with minimal outlay on labour and with costs reduced to the minimum.

Surprisingly, this object is achieved by a process for the colouring of ceramics in the porous or absorbent state, which is characterized in that the ceramics are translucent and metal ion solutions or metal complex solutions are used for the colouring. Solutions preferred for this contain defined concentrations of at least one of the salts or complexes of the rare earth elements or the elements of the subgroups.

DETAILED DESCRIPTION

The solutions are preferably water- or alcohol-based. Suitable salts or complexes are preferably those from the group of the rare earths or the 2nd or 8th subgroups, in particular Pr, Er, Fe, Co, Ni, Cu.

Salts or complexes with inorganic opposed ions such as e.g. $Cl^-$, $Br^-$, $J^-$, $SO_4^{2-}$, $SO_3^{2-}$, $NO_2^-$, $NO_3^-$, $ClO_4^-$, $ONC^-$, $SCN^-$, are preferred, which can also mean oxo complexes of acid or basic salts, but not double salts with an element of the 1st or 2nd main groups. Furthermore, salts or complexes with organic ions or ligands are preferred which contain 1 to 30 C atoms and from 1 to 10 heteroatoms, such as O, N, S. In detail, these are alkoxides or salts of organic acids. Preferred here among the alkoxides are the salts of the $C_1$-$C_{10}$-alkanols, in particular the methoxides, ethoxides, n- and i-proproxides and n-, i-, sec. or tert.-butoxides. Among the salts of organic acids, those of mono-, di- and tri-$C_1$-$C_{20}$-carboxylic acids are preferred, in particular formate, acetate, malate, maleate, maleinate, tartate, oxalate. Finally, the ligands are also taken to include complexing agents serving to stabilise the metal salts in their oxidation stage and in solution. These can be organic $C_2$-$C_{20}$ molecules with up to 10 hetero atoms, O, N or S, including in particular EDTA and its salts, NTA, salicylic acid, phenols, 5-sulphosalicylic acid etc.

Aqueous or alcoholic solutions of Pr, Er, Fe, are preferred, for example as chlorides, acetates or alcoholates.

The ions or complexes are preferably used in concentrations of 0.0001 to 15 wt.-%, particularly preferably from 0.001 to 10 wt.-% and quite particularly preferably from 0.01 to 7 wt.-%.

By ceramics and dental ceramics are meant here all high-strength oxides of the elements of the main groups II, III and IV and the subgroups III and IV as well as their mixtures, in particular $Al_2O_3$, $ZrO_2$, both partly and also fully stabilised, MgO, $TiO_2$ and their mixtures. In particular, translucent ceramics are taken to be covered by the term ceramics and dental ceramics.

Furthermore it is surprising that the depth of colour of the colouring is not dependent on the action time of the solution but only on its concentration. This is particularly advantageous, as the dental technician is not tied to action times accurate to within a few seconds, but can perform his work within certain tolerances for as long as is desired with the solutions according to the invention. The action time of the solution can in theory be as long as desired. It depends only on other effects in the solution, for example pH-value changes or the release of ions, which can hinder the colouring process. The result is generally an action time, until the depth of colour of the colouring does not change, of a few hours. The action time is preferably under 2 hours, in particular under 1 hour and particularly preferably under 20 minutes.

Advantageously, the above mentioned intermediate layer (y) can be completely dispensed with thanks to the present invention, as the framework ceramic can already be individually coloured by the solutions according to the invention. An additional cost- and time-intensive step of the firing of the intermediate layer is therefore dispensed with. Only the free path length z=x+y+m is available to the incident light, as the path is no longer interrupted by the intermediate light.

The solutions according to the invention can also contain, alongside the salts or complexes of the rare earth elements or the subgroup elements, stabilising agents, such as complexing agents, grinding auxiliaries as well as organic dye stuff pigments to facilitate the matching of the colour by the dental technician.

Complexing agents, such as ethylenediaminetetra acetic acid, are suitable as stabilising agents. Grinding auxiliaries are taken to include for example temporary binders and thixotropy agents, such as polyglycols, polysaccharides, polyethylene glycols, polyvinyl alcohols, hydrogenated castor oils.

Due to the low concentrations of colouring ions or complexes within the solutions according to the invention and the associated poor optical recognizability of the applied shade, organic pigments can also be added to facilitate the matching of colour by the dental technician. These additives are particularly helpful during the application of the solutions to specific areas by means of application instruments. The additives are to be chosen so that they are destroyed without leaving any residue upon the firing of the prosthetic work.

The solutions according to the invention can be applied in the following ways to the pre-sintered or absorbent ceramics:
1. Immersion of the ceramic in solutions of defined concentrations;
2. Deposition of the solutions to the ceramic by means of suitable application instruments, for example, brush, swab;
3. Deposition of the solutions to the ceramic by means of spraying processes.

Wall thicknesses of up to 10 mm, preferably 7 mm, are thoroughly coloured by means of the process according to the invention. In particular in the dental field, dimensions of 10 mm, preferably 7 mm, for the diameter of a workpiece and 7 mm, preferably 5 mm, for the height of a workpiece are possible in the preparation of crowns and bridges. These mm values relate to the thicknesses of the colourable wall thickness of the dental workpieces. Naturally, workpieces outside the limits given here are also contained in the scope of the invention.

The ceramics are preferably completely through-coloured.

The invention also relates to a kit, comprising
(i) at least one stock bottle with a metal ion or metal complex solution for the colouring of the ceramics,
(ii) a receptacle for the colouring, and
(iii) optionally a screen.

The invention is explained in detail in the following by means of examples, without thereby limiting it.

Concentration-dependent Colouring of Zirconium Oxide Stabilised by 3 mol Yttrium Oxide For the preparation of the solutions, the corresponding amounts of colour reagent are dissolved in water. Ceramic bodies are steeped in this for 5 minutes and then dried and sintered. The specimens are then ground and polished for the colorimetry. The following parameters form the basis of the colour determination:

Opacity value O: Measure of the transparency (0% is completely transparent, 100% is opaque),
$L^*$-value: Brightness (100: complete reflection; 0; no reflection);
$a^*$-value: Red-green shift (+a: red; −a: green);
$b^*$-value: yellow-blue shift (+b: yellow; −b: blue);
Measuring apparatus: Hunterlab LabScan Spectrocolorimeter; Measurement method: Cielab (colour), opacity according to ASTM D2805/TAPPI T425/TAPPI T519.

To demonstrate the independence of the colour intensity from the action time of the solution, various action times are used with a fixed solvent concentration and the colour determination carried out analogously.

Commercial zirconium dioxide from Tosoh, Japan of the type TZ3YE was used as material.

Colouring With $Fe(III)Cl_3$ Solutions

| Concentration solution [wt. - %] | $L^*$ | $a^*$ | $b^*$ | O |
|---|---|---|---|---|
| 0 | 85.67 | −0.97 | 1.51 | 91.4 |
| 0.1 | 83.93 | −1.67 | 5.15 | 92.36 |
| 0.3 | 79.04 | −1.52 | 22.35 | 95.1 |
| 0.5 | 75.37 | 1.16 | 25 | 95.32 |
| 0.75 | 74.01 | 1.72 | 25.91 | 96.51 |
| 1 | 72.25 | 2.83 | 24.67 | 97.79 |

Colouring With Pr(III) Acetate Solutions

| Concentration solution [wt. - %] | $L^*$ | $A^*$ | $b^*$ | O |
|---|---|---|---|---|
| 0.1 | 81.02 | −3.60 | 24.98 | 89.98 |
| 0.25 | 80.80 | −3.02 | 34.17 | 91.40 |
| 0.75 | 74.85 | 4.77 | 47.31 | 92.11 |

Result: The intensity of the colour can be controlled via the concentration of the solution.

Dependency of Colour Intensity on Action Time

Solution concentration: 0.75 wt.-% Fe (III) Cl solution

| Action time | $L^*$ | $a^*$ | $b^*$ | O |
|---|---|---|---|---|
| 2 minutes | 75.18 | 0.32 | 20.15 | 96.05 |
| 5 minutes | 76.06 | −0.42 | 21.4 | 95.86 |
| 10 minutes | 75.18 | −0.09 | 22.4 | 96.08 |
| 20 minutes | 75.80 | −0.21 | 23.11 | 96.37 |

Result: The action time has no effect on the colour intensity.

What is claimed is:
1. A process for coloring translucent dental ceramics which comprises:
providing a pre-sintered dental ceramic;
applying at least one of a metal ion coloring solution or metal complex coloring solution to the pre-sintered ceramic to form an intermediate product; and
sintering the intermediate product to form a translucent, colored dental ceramic.
2. The process according to claim 1, wherein the solutions contain at least one of the ions or complexes of the rare earth elements or subgroups II and VIII of the Periodic Table and copper.

3. The process according to claim 2, wherein the ions or complexes are at least one salt or complex selected from the group consisting of chlorides, acetates, alcohols and oxo complexes.

4. The process according to claim 1, wherein the solutions contain at least one of Pr, Er, Fe, Co, Ni or Cu.

5. The process according to claim 1, wherein ceramics based on zirconium oxide or aluminum oxide are used.

6. The process according to claim 1, wherein the ion or complex solutions are water-based or alcohol-based.

7. The process according to claim 1, wherein an action time of the ion or complex solutions is under two hours.

8. The process according to claim 7, wherein the action time is under 1 hour.

9. The process according to claim 7, wherein the action time is under 20 minutes.

10. The process according to claim 1, wherein the concentration of the solutions is 0.001 to 15 wt. %.

11. The process according to claim 1, wherein the coloring takes place by immersion of the ceramic in the solutions, deposition of the solutions to the ceramic with the help of application instruments or by spraying of the solutions onto the ceramic.

12. The process according to claim 1, wherein the ceramics to be colored have a diameter of 10 mm and a height of 7 mm.

13. The process according to claim 1, wherein the ceramics are completely through-colored.

14. The process according to claim 1, wherein the ceramics to be colored have a diameter of 7 mm and a height of 5 mm.

* * * * *

UNITED STATES PATENT AND TRADEMARK OFFICE
CERTIFICATE OF CORRECTION

PATENT NO. : 6,709,694 B1
DATED : March 23, 2004
INVENTOR(S) : Suttor, Daniel

It is certified that error appears in the above-identified patent and that said Letters Patent is hereby corrected as shown below:

Column 1,
Line 57, delete "□" and insert -- α --, therefor.

Column 2,
Line 18, delete "$SO_4,^{2-}$" and insert -- $SO_4^{2-}$ --, therefor.

Signed and Sealed this

Thirtieth Day of August, 2005

JON W. DUDAS
*Director of the United States Patent and Trademark Office*

(12) EX PARTE REEXAMINATION CERTIFICATE (6153rd)
United States Patent
Suttor et al.

(10) Number: US 6,709,694 C1
(45) Certificate Issued: Mar. 11, 2008

(54) COLORING CERAMICS BY WAY OF IONIC OR COMPLEX-CONTAINING SOLUTIONS

(75) Inventors: Daniel Suttor, Seefeld (DE); Holger Hauptmann, Sindelsdorf (DE); Robert Schnagl, Landsberg (DE); Sybille Frank, Seefeld (DE)

(73) Assignee: 3M ESPE AG, Seefeld (DE)

Reexamination Request:
No. 90/007,990, Apr. 3, 2006

Reexamination Certificate for:
| | |
|---|---|
| Patent No.: | 6,709,694 |
| Issued: | Mar. 23, 2004 |
| Appl. No.: | 09/890,690 |
| Filed: | Sep. 26, 2001 |

Certificate of Correction issued Aug. 30, 2005.

(22) PCT Filed: Feb. 4, 2000
(86) PCT No.: PCT/EP00/00910
§ 371 (c)(1),
(2), (4) Date: Sep. 26, 2001
(87) PCT Pub. No.: WO00/46168
PCT Pub. Date: Aug. 10, 2000

(30) Foreign Application Priority Data
Feb. 4, 1999 (DE) .......................... 199 04 522

(51) Int. Cl.
| | |
|---|---|
| A61K 6/04 | (2006.01) |
| A61K 6/06 | (2006.01) |
| A61K 6/02 | (2006.01) |
| A61K 6/083 | (2006.01) |
| C04B 41/45 | (2006.01) |
| C04B 41/85 | (2006.01) |
| C04B 41/50 | (2006.01) |
| A61C 13/08 | (2006.01) |

(52) U.S. Cl. ............... 427/2.26; 427/2.1; 427/2.27; 427/372.2; 427/376.3; 427/443.2; 427/431; 427/376.2; 427/2.29; 427/2.24; 433/203.1

(58) Field of Classification Search ............ None
See application file for complete search history.

(56) References Cited

U.S. PATENT DOCUMENTS

| | | | |
|---|---|---|---|
| 4,189,325 A | * | 2/1980 | Barrett et al. ............... 106/35 |
| 5,219,805 A | | 6/1993 | Yoshida et al. |
| 5,263,858 A | | 11/1993 | Yoshida et al. |
| 6,132,672 A | | 10/2000 | Vignali |
| 6,709,694 B1 | | 3/2004 | Suttor et al. |

FOREIGN PATENT DOCUMENTS

| | | | |
|---|---|---|---|
| DE | 2012304 | | 9/1971 |
| EP | 47873 A2 | * | 3/1982 |
| EP | 0 389 461 B1 | | 9/1990 |
| EP | 0 816 305 A1 | | 1/1998 |
| JP | 3-5366 A | | 1/1991 |
| JP | 3-170148 A | | 7/1991 |
| JP | 3-198841 | | 8/1991 |
| JP | 4-280864 A | | 10/1992 |
| JP | 8-33650 A | | 2/1996 |
| JP | 9-110563 | | 4/1997 |
| JP | 9-142966 | | 6/1997 |

OTHER PUBLICATIONS

Cales, *Colored Zirconia Ceramics for Denal Applications*, Bioceramics, vol. 11, 1998, 3 Sheets.

Rieger, "Aluminum and Zirconium Oxide Ceramics in Medicine"; Industrie Diamanten Rundschau, IDR 2, 1993, pp. 1–7.

* cited by examiner

*Primary Examiner*—Stephen Stein

(57) ABSTRACT

The invention relates to the coloring of ceramics by means of ionic or complex-containing solutions. Solutions preferred for this contain defined concentrations of at least one of the salts or complexes of the rare earth elements or the elements of the subgroups. The invention also relates to a kit, which comprises at least one stock bottle with such a coloring solution, a receptacle for the coloring as well as optionally a screen.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–14, dependent on an amended claim, are determined to be patentable.

New claims 15–30 are added and determined to be patentable.

1. A process for coloring translucent dental ceramics which comprises:
   providing a pre-sintered dental ceramic *workpiece*;
   applying at least one of a metal ion coloring solution or metal complex coloring solution to the pre-sintered ceramic *workpiece* to form an intermediate product; and
   sintering the intermediate product to form a translucent, colored dental ceramic *workpiece*.

15. *A process for coloring translucent dental ceramics which comprises:*
    *providing a pre-sintered dental ceramic;*
    *applying at least one of a metal ion coloring solution or metal complex coloring solution to the pre-sintered ceramic to form an intermediate product; and*
    *sintering the intermediate product to form a translucent, colored dental ceramic, wherein the color of the translucent, colored dental ceramic matches a desired tooth color.*

16. *The process according to claim 15, wherein the pre-sintered dental ceramic is a dental workpiece useful for the preparation of a dental prosthesis.*

17. *The process according to claim 15, wherein the pre-sintered dental ceramic is a dental framework for a crown or bridge.*

18. *The process according to claim 15, wherein the translucent, colored dental ceramic is a dental prosthetic article.*

19. *The process according to claim 18, wherein the dental prosthetic article is a crown or bridge.*

20. *The process according to claim 18, wherein the dental prosthetic article is a dental framework for a crown or bridge.*

21. *The process according to claim 18, wherein the coloring solution comprises iron (Fe).*

22. *A process for coloring translucent dental ceramics which comprises:*
    *providing a pre-sintered dental ceramic framework;*
    *applying at least one of a metal ion coloring solution or metal complex coloring solution to the pre-sintered ceramic framework to form an intermediate product; and*
    *sintering the intermediate product to form a translucent, colored dental ceramic framework.*

23. *The process according to claim 22, wherein the translucent, colored dental ceramic framework is a crown or bridge framework.*

24. *The process according to claim 22, wherein the color of the translucent, colored dental ceramic matches a desired tooth color.*

25. *The process according to claim 22, wherein the coloring solution comprises iron (Fe).*

26. *A process for coloring translucent dental ceramics which comprises:*
    *providing a pre-sintered dental ceramic workpiece;*
    *applying at least one of a metal ion coloring solution or metal complex coloring solution to the pre-sintered ceramic workpiece to form an intermediate product; and*
    *processing and sintering the intermediate product to form a translucent, colored dental ceramic prosthetic article.*

27. *The process according to claim 26, wherein the dental prosthetic article is a crown or bridge.*

28. *The process according to claim 26, wherein the dental prosthetic article is a dental framework for a crown or bridge.*

29. *The process according to claim 26, wherein the color of the translucent, colored dental ceramic matches a desired tooth color.*

30. *The process according to claim 26, wherein the coloring solution comprises iron (Fe).*

* * * * *

(12) INTER PARTES REEXAMINATION CERTIFICATE (593rd)

United States Patent
Suttor et al.

(10) Number: US 6,709,694 C2
(45) Certificate Issued: May 2, 2013

(54) COLORING CERAMICS BY WAY OF IONIC OR COMPLEX-CONTAINING SOLUTIONS

(75) Inventors: Daniel Suttor, Seefeld (DE); Holger Hauptmann, Sindelsdorf (DE); Robert Schnagl, Landsberg (DE); Sybille Frank, Seefeld (DE)

(73) Assignee: 3M ESPE AG, Seefeld (DE)

Reexamination Request:
No. 95/000,390, Aug. 13, 2008

Reexamination Certificate for:
Patent No.: 6,709,694
Issued: Mar. 23, 2004
Appl. No.: 09/890,690
Filed: Sep. 26, 2001

Reexamination Certificate C1 6,709,694 issued Mar. 11, 2008

Certificate of Correction issued Aug. 30, 2005

(21) Appl. No.: 95/000,390

(22) PCT Filed: Feb. 4, 2000

(86) PCT No.: PCT/EP00/00910
§ 371 (c)(1),
(2), (4) Date: Sep. 26, 2001

(87) PCT Pub. No.: WO00/46168
PCT Pub. Date: Aug. 10, 2000

(30) Foreign Application Priority Data

Feb. 4, 1999 (DE) .................................. 199 04 522

(51) Int. Cl.
| | | |
|---|---|---|
| *A61K 6/04* | (2006.01) | |
| *A61K 6/06* | (2006.01) | |
| *A61K 6/02* | (2006.01) | |
| *C04B 41/50* | (2006.01) | |
| *C04B 41/85* | (2006.01) | |
| *C04B 41/45* | (2006.01) | |

(52) U.S. Cl.
USPC ......... 427/2.26; 427/2.1; 427/2.24; 427/2.27; 427/2.29; 427/372.2; 427/376.2; 427/376.3; 427/431; 427/443.2; 433/203.1

(58) Field of Classification Search
None
See application file for complete search history.

(56) References Cited

To view the complete listing of prior art documents cited during the proceeding for Reexamination Control Number 95/000,390, please refer to the USPTO's public Patent Application Information Retrieval (PAIR) system under the Display References tab.

*Primary Examiner* — Krisanne Jastrzab

(57) ABSTRACT

The invention relates to the coloring of ceramics by means of ionic or complex-containing solutions. Solutions preferred for this contain defined concentrations of at least one of the salts or complexes of the rare earth elements or the elements of the subgroups. The invention also relates to a kit, which comprises at least one stock bottle with such a coloring solution, a receptacle for the coloring as well as optionally a screen.

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 4, 21, 25 and 30 is confirmed.

Claims 1-3, 5-20, 22-24 and 26-29 are cancelled.

New claims 31-38 are added and determined to be patentable.

*31. The process according to claim 1, wherein the solutions contain at least one of the ions or complexes of the rare earth elements or subgroup VIII of the Periodic Table and copper.*

*32. The process according to claim 1, wherein the solutions contain iron (Fe).*

*33. The process according to claim 15, wherein the solution contains at least one of the ions or complexes of the rare earth elements or subgroup VIII of the Periodic Table and copper.*

*34. The process according to claim 15, wherein the solution contains at least one of Pr, Er, Fe, Co, Ni or Cu.*

*35. The process according to claim 22, wherein the solution contains at least one of the ions or complexes of the rare earth elements or subgroup VIII of the Periodic Table and copper.*

*36. The process according to claim 22, wherein the solution contains at least one of Pr, Er, Fe, Co, Ni or Cu.*

*37. The process according to claim 26, wherein the solution contains at least one of the ions or complexes of the rare earth elements or subgroup VIII of the Periodic Table and copper.*

*38. The process according to claim 26, wherein the solution contains at least one of Pr, Er, Fe, Co, Ni or Cu.*

* * * * *